US010815521B1

United States Patent
Saraf et al.

(10) Patent No.: US 10,815,521 B1
(45) Date of Patent: Oct. 27, 2020

(54) ELECTROCHEMICAL MICROARRAY CHIP AND APPLICATIONS THEREOF

(71) Applicants: Ravi Saraf, Lincoln, NE (US); Abhijeet Prasad, Atlanta, GA (US); Shobana Raghunath, Lincoln, NE (US); Rahul Tevatia, Lincoln, NE (US)

(72) Inventors: Ravi Saraf, Lincoln, NE (US); Abhijeet Prasad, Atlanta, GA (US); Shobana Raghunath, Lincoln, NE (US); Rahul Tevatia, Lincoln, NE (US)

(73) Assignee: Ravi Saraf, Lincoln, NE (US)

( * ) Notice: Subject to any disclaimer, the term of this patent is extended or adjusted under 35 U.S.C. 154(b) by 225 days.

(21) Appl. No.: 15/919,075

(22) Filed: Mar. 12, 2018

Related U.S. Application Data

(60) Provisional application No. 62/470,536, filed on Mar. 13, 2017, provisional application No. 62/585,514, filed on Nov. 13, 2017.

(51) Int. Cl.
*G01N 27/447* (2006.01)
*C12Q 1/6816* (2018.01)
(Continued)

(52) U.S. Cl.
CPC ..... *C12Q 1/6816* (2013.01); *G01N 27/44713* (2013.01); *G01N 27/44756* (2013.01); *G01N 27/49* (2013.01); *B03C 5/005* (2013.01)

(58) Field of Classification Search
CPC ........... G01N 27/447; G01N 27/44704; G01N 27/44713; G01N 27/44756; G01N 27/453; B03C 5/005
See application file for complete search history.

(56) References Cited

U.S. PATENT DOCUMENTS 4,794,086 A * 12/1988 Kasper ............... G01N 15/06
356/335
6,391,624 B1 * 5/2002 Megerle ............... C12Q 1/6825
422/68.1
(Continued)

FOREIGN PATENT DOCUMENTS

WO WO 2009/107614 A1 * 9/2009 ............... C12Q 1/68

OTHER PUBLICATIONS

Raghunath et al., "Quantitative Electrochemical DNA Microarray on a Monolith Electrode with Ten Attomolar Sensitivity, 100% Specificity, and Zero Background," ChemElectroChem Feb. 1, 2018:5(3): 429-433 with Supporting Information, unpaginated, appended (published online Dec. 14, 2017) (Year: 2017).*
(Continued)

*Primary Examiner* — Alexander S Noguerola
(74) *Attorney, Agent, or Firm* — William L. Botjer

(57) ABSTRACT

An electrochemical microarray chip to detect specific sequences of single-stranded DNA (ssDNA) or single-stranded RNA (ssRNA) target molecules in solution using a microarray of microspots of probe molecules immobilized on an electrode. The chip pertains to both regulating the immunospecific binding to the array of probes on the electrode and their subsequent detection on the microarray spots on the monolith electrode by electrochemical methods. The device can quantitatively measure the concentration of target molecules of specific sequence at high specificity and high sensitivity.

15 Claims, 14 Drawing Sheets

(51) Int. Cl.
*G01N 27/49* (2006.01)
*B03C 5/00* (2006.01)

(56) References Cited

U.S. PATENT DOCUMENTS

2006/0166216 A1* 7/2006 Nakao ................ G01N 33/5438
435/6.11
2011/0100820 A1* 5/2011 Bachmann ........ B01L 3/502761
204/547

OTHER PUBLICATIONS

Tlili et al., "Electrochemical impedance probing of DNA hybridization on oligonucleotide-functionalised polypyrrole," Talanta 68 (2005) 131-137 (Year: 2005).*

* cited by examiner

ELECTROCHEMICAL MICROARRAY CHIP AND APPLICATIONS THEREOF

This application claims priority from U.S. provisional application Ser. No. 62/470,536 filed Mar. 13, 2017 and U.S. provisional application Ser. No. 62/585,514 filed Nov. 13, 2017.

This application hereby incorporates by reference the disclosures of U.S. patent application Ser. No. 15/916,963 filed Mar. 9, 2018 and U.S. Pat. No. 7,826,060 as if fully set forth herein.

BACKGROUND OF THE INVENTION

1. Field of the Invention

The present invention relates to measuring specific target sequences of single stranded DNA (ssDNA) or single-stranded RNA (ssRNA) molecules in a solution by detecting their specific binding to a microarray of microspots with different sequences of tethered probe molecules immobilized on an electrode. The probes may be ssDNA, ssRNA, or peptide nucleic acid (PNA). The process to immobilize the probe molecules on the electrode is not limited to the invention. Several immobilization processes are documented in the literature, which for the invention, constitute standard methods practiced in the art. The invention pertains to a chip with at least two isolated electrodes with each having similar or different kinds of microarrays of immobilized probes. The microarray has at least two microspots with different types of immobilized probe sequences. The probes may be ssDNA, ssRNA, or peptide nucleic acid (PNA) of base sequences that are complementary to at least one target sequence over at least contiguous bases. The electrode surface after immobilization of the microarray should be at least 50% reflective at the wavelength of the laser light, preferably 90% reflective. The probe molecules may be comprised of 10 to 1,000 base sequences, preferably 10 to 70 base sequences. The target molecules may be comprised of 10 to 1,000 base sequences, preferably 10 to 200 base sequences.

The invention pertains to binding the target molecule in the solution to the immobilized probe using oscillatory potential, E', applied between the electrode and the solution over a range of potential. The sequence lengths where the probe and target molecules specifically bind are at least 5 contiguous base pairs, preferable 10 to 100 contiguous base pairs. The complementary contiguous sequences of the probe and target molecules for specific binding may be at any relative location on the two molecules. Specifically in the invention, a redox ion is dissolved in the solution where some of the said ions oxidize at the electrode surface while the target molecules are being attracted to the electrode. The role of the redox ion is to enhance and regulate binding kinetics. The invention pertains to regulating the level of probe-target binding on each electrode of the chip by applying different oscillatory conditions.

The invention pertains to measuring the different level of binding of target molecules to a microarray of probe molecules on each electrode. Specifically, the invention pertains to measuring the binding on every microspot of the microarray on each electrode by scanning a laser beam to measure differential reflectivity due to a fast AC potential at frequency $\omega$ as a function of a slow oscillatory potential, E, both applied between the solution and the electrode. The slow potential, E is at least 10-fold, preferably more than 100-fold slower than the AC potential. The change in specific binding of the target sequence to the complementary probe microspot is obtained by measuring the amplitude of differential reflectivity at $\omega$ due to AC potential as a function of applied slow potential, E. From the change in binding level measured by differential reflectivity as a function of applied oscillatory potential to cause binding, the relative level of the said target concentration may be estimated. The signal of change in differential reflectivity at $\omega$ is enhanced by including a redox ion that specifically binds to the complimentary binding site and the potential for redox is within the range of applied oscillatory potential, E. The redox ion may be in the solution or tethered to the probe molecules. The solvent of the solution is an organic solvent that can dissolve ions. The method is sensitive to measuring 0.1 femtomolar (fM) of target molecules in a solution.

2. Description of Related Art

Target ssDNA and ssRNA are specific fragments of genomic material obtained from biological samples, such as cells, blood, urine, sweat, saliva, tissue, and other sources, in a living system. The specific segments are highly regulated digestive products of the genomic material utilizing standard molecular biology methods, such as restriction enzymes, well known in the art. Sequencing the targets leads to a variety of information, such as early detection of diseases, efficacy of a drug or a treatment, and molecular mechanism of biological processes. Typically, the analysis requires sequencing of multiple ssDNA and ssRNA targets obtained from the biospecimen.

Microarray technology is a well-established, highly multiplexed method for sequencing using fluorescence labels. A more expensive technology developed recently is next generation sequencing (NGS) which also uses fluorescent labels. Several methods of investigating specific binding without using labels have been developed owing to a large change in the refractive index between ssDNA and dsDNA. The change in the refractive index is large enough to obtain attomole responsivity by optical methods using interferometry, surface plasmon resonance, ellipsometry, and an optical resonator.

Another class of devices and the subject of the current patent are electrochemical methods to detect specific binding. A promising electrochemical detection approach is to use the redox signal from an intercalating (redox) dye (such as methylene blue (MB)) that specifically binds to regions of specific binding between the probe and the target. The redox current from the dye is proportional to the relative concentration of the target ssDNA.

Using a large electrode to measure one probe-target binding per electrode, Barton invented an electrochemical method to measure binding using MB (Barton et al., U.S. Pat. No. 6,221,586 B1). Saraf developed an interferometer to measure local redox reaction to obtain specific binding (Saraf et al. U.S. Pat. No. 7,826,060 B2). Hill developed an enzyme-mediated electrochemical method to measure binding (Hill et al., U.S. Pat. No. 4,840,893). Reacting the nucleic acid with a transition metal complex, Thorp developed a method to electrochemically detect specific binding (Thorp et al., U.S. Pat. No. 5,871,918). Henkens developed an amperometric electrochemical method to measure current on binding (Henkens et al., U.S. Pat. No. 6,391,558 B1). Using a soybean peroxidase (SBP) enzyme-labeled target, de Lumley-Woodyear developed an electrochemical method to measure binding (de Lumley-Woodyear et al., US 2002/0081588 A1). Sun developed a detection system to measure binding using a field-effect transistor incorporated with nanochannels (Sun et al., US 2011/0236984 A1). All of the above methods do not describe a differential reflectivity method to measure local binding.

Several designs using electrochemical methods have been developed to enhance binding. Ryu reported a method to apply an electric field in DNA containing solution to deposit DNA molecules on poly(methyl methacrylate) film (Ryu et al. US 2013/0078386 A1). Szalay developed a method for translocation of DNA in plant cells by applying an electric field in DNA containing solution in contact with plant cells (Szalay et al., WO 1987/006614 A1). Choong invented a method to enhance bioconjugation by applying an electric field in the solution and inserting the sample in the field to deposit molecules with no current flow (Choong et al., U.S. Pat. No. 6,238,909 B1). Mirkin developed a method to enhance binding of DNA oligomers coated on nanoparticles (Mirkin et al., US 2002/0172953 A1). Blackburn developed a method to accelerate capture of target analyte ligands to a surface by applying an electric field and detecting the said analyte by electron transfer (Blackburn et al., U.S. Pat. No. 6,264,825 B1). In all of the above-mentioned methods, the concept of the present invention to discharge the interfacial layer by redox ion to promote probe-target binding and optically measure amount of probe-target binding has not been described.

SUMMARY OF THE INVENTION

The invention pertains to a device to detect multiple segments of target ssDNA and ssRNA obtained from biological samples. The approach is based on the well known microarray analysis using fluorescent labels to measure the levels of binding of various target sequences to their complementary probes immobilized on an array of microspots. Specifically, the present invention relates to enhancing and regulating the kinetics of probe-target binding to more than one set of microarrays of probe molecules and measuring the relative level of binding on each microarray on the chip. Typically, the various microarrays subjected to different binding conditions on the chip may have the set of microspots of the same probe molecules. Typically, fresh target solution may be inserted for binding on each individual electrode. The resultant information obtained is on the binding level of various target sequences to a complementary probe as a function of applied binding condition. The said information on amount of binding as a function of binding condition for multiple target sequence complementary to various probe molecules in the microarray may be analyzed to profile relative concentration of the various said target sequences. Specifically, the invention pertains to a chip with the capability to control the level of specific binding of a particular target to said microspots with a complementary probe by regulating the electric field to affect specific binding. The invention further pertains to measuring the level of specific binding on each microspot of the microarray on each of the electrodes on the chip. The invention pertains to performing the binding and detection using an electrochemical method on a chip with more than one electrode. The method can be multiplexed to obtain information on multiple target sequences by immobilizing a microarray on different electrodes on the chip with microspots of probes of different sequences that are complementary probes to each target.

The invention pertains to a chip comprised of one or more isolated electrodes with an array of microspots of tethered probe molecules immobilized on each electrode. Typically, the isolated electrodes are patterned on a chip with an electrical circuit to connect each individual electrode to a power supply. The chip may be a rigid substrate with an insulating surface to ensure that the electrodes are isolated from each other and with circuit lines to allow interconnection to electronics for power and signal for each electrode. The electrode and circuit lines may be fabricated using standard techniques developed for Si technology, such as photolithography. The substrate may be a rigid material, such as a ceramic or a glass. The details of the fabrication of the chip are not limited to the invention. A well-known example to an expert in the art is a chip comprised of Si with a passivation layer of $SiO_2$ as a substrate. The electrode may be a conducting material that can facilitate a redox reaction. The electrode surface should allow proper modification to tether the probe molecules on the surface using one of their ends. The electrode surface with the modification should be at least 50% reflective at the wavelength of the laser light, preferably 90% reflective. The electrode material, its patterning, and its circuitization is not limited to the invention so along as it can facilitate redox reaction, allow immobilization of probe molecules, adhere to the underlying insulating substrate, allow proper packaging to apply independent potential on each electrode while in contact with fluid without electrical shorting, and is highly reflective. An example would be a thin film of Au deposited on $SiO_2/Si$ substrate with an adhesion layer of a reactive metal, such as Cr. The probe molecules may be ssDNA or ssRNA with 10 to 1,000 base sequences, preferably 10 to 200 bases. The sequence lengths where the probe and target molecules specifically bind are at least 5 contiguous base pairs, preferable 10 to 100 contiguous base pairs. The complementary contiguous sequences of the probe and target molecules for specific binding may be at any relative location on the two molecules. It is preferred that the complementary contiguous sequence of the probe and target molecules for specific binding be closer to the tethered end of the probe molecule for better electron exchange. It is well known to experts in the art that the complementary sequences between ssDNA or ssRNA target to ssDNA, ssRNA, and PNA probe are defined by the hydrogen bonding characteristics of the base pairs. The process to immobilize the probe molecules on the electrode is not limited to the invention. Several immobilization processes are documented in the literature, which for the invention constitute standard methods practiced in the art. A practice well appreciated to those expert in the art is to have a reactive terminal group at one end of the probe molecule and a complementary reactive group on the modified electrode to obtain bioconjugation. For example, the probe molecules may be immobilized onto a Au or Pt or Ag electrode by incorporating a thio-group at one end of the probe molecular chain.

Generally, the electrode is a material that has a conducting surface on which the probe molecules can be immobilized. The immobilization may be by a covalent bond, hydrogen bond, an electrostatic interaction, or an absorption by dispersive interaction. The electrode is preferably inert that does not etch or tarnish during the EFIB process. Examples of the electrode may be Au, Pt, Ag, Re, Ru, and Rh and their alloys. The electrode may also be composed of carbon materials such as carbon nanotubes, graphene, or form of graphite. The electrode may be composed of conducting polymers or blend of conducting polymer. The electrode may be a composite of conducting powder mixed with polymer matrix. The electrode may be a composite or alloys of metals, inorganics and organics as long as the surface is conducting, the material is to be inert to withstand the binding process, and the probe molecules can be immobilized. The top surface of the electrode remains conducting and relatively inert over at least two periodic cycles of the potential.

The invention expands on a submitted patent application for a device to electrochemically enhance probe-target binding by incorporating a redox ion (U.S. patent application Ser. No. 15/916,963 filed Mar. 9, 2018 Hereinafter referred to as "EFIB"). Specifically, the invention expands on the said submitted application to regulate the binding from a low amount of binding to a high amount of binding. The process is called electric field influenced binding (EFIB). Briefly, the invention pertains to binding the target molecule in the solution to the immobilized probe using oscillatory potential over a range of potential, $\Delta E'$. The shape of the periodic oscillation of the potential may be a simple sinusoidal to a complex pulse shape. Typically, the complex pulse shapes may be, for example, a square-pulse, a triangular-pulse, a Gaussian-pulse, or their combination. Specifically, the invention is to regulate the binding kinetics by incorporating at least one type of redox ion of equilibrium redox potential of $E°$ in the solution that undergoes reaction, where at least one electron is exchanged with the said electrode. It is preferred that the said ion undergoes an oxidation reaction within the range of $\Delta E'$. It is further preferred that the said ion undergoes partial or complete oxidation for $E'>0$ while the negatively charged target molecules are being attracted towards the electrode. It is further preferred that the range of the oscillatory potential must be wide enough to regenerate the interfacial layer by both repelling the unattached target molecules and reducing the oxidized ions. Thus, it is preferred that $\Delta E'$ spans from $E'>0$ to promote binding to $E'<0$ to regenerate the interfacial layer. The range, shape, and frequency of the oscillatory potential may significantly affect the binding kinetics. The range, shape, and frequency of the oscillatory potential may significantly affect the specificity of probe-target binding. Typically, the range, shape, and frequency of the oscillatory potential will be kept constant while the number of cycles, N, will be varied electrode-to-electrode on the chip to regulate the level of binding to a microarray on each electrode.

The invention pertains to regulating the level of probe-target binding on each electrode of the chip from a low to a high amount by applying different oscillatory conditions. One convenient, but not limiting, approach to regulating binding on each electrode is by applying an oscillatory potential of fixed range, shape, and frequency, with a different number of cycles, N. It is expected that by regulating N, the amount of binding can be controlled. An intuitive result is that electrodes subjected to larger N will have more binding; and at some large N, the level of binding will saturate. In one specific approach, for example, a chip may have K electrodes with the same microarray design where the microspots are comprised of a variety of the same probe molecules complementary to different target sequences. Subjecting each electrode to different N, data corresponding to a binding level for each target, as a function of N over the K electrodes, may be obtained. One intuitive result is that for targets with high concentrations, some binding will be observed at low N while the levels may saturate for high N; for low concentrations there may be no binding at low N, and the signal would not reach saturation at high N; while in the medium range the behavior of the binding level as a function of N may be intermediate. The analysis of the behavior may lead to quantification of relative levels of target concentration.

The invention expands on a issued U.S. patent on a device to measure differential reflectivity from an electrode surface subjected to electrochemical stimulus (U.S. Pat. No. 7,826,060). The instrument is called scanning electrometer for electrical double layer (SEED). Specifically, the invention expands on the said submitted application to determine the relative concentration of target molecules by obtaining the relative level of binding on each microspot of the array on all the electrodes on the chip that are subjected to different binding conditions. Briefly, the invention pertains to measuring the level of binding on each microspot of the array for each electrode by scanning a laser beam to measure differential reflectivity. The differential reflectometry is performed by measuring the amplitude of the reflectivity due to an AC potential at frequency $\omega$ as a function of applied oscillatory potential, E. All the potential are applied between the electrode and the solution. The principle of the invention is to measure amplitude of oscillatory reflectivity at $\omega$ due to the AC potential. Subsequently in the invention the amplitude of reflectivity also called differential reflectivity will be simply referred to as reflectivity. The solution contains a molecule that specifically binds to certain regions of probe-target duplex and the said molecule can under redox reaction at the electrode. An example would be methylene blue (MB) that binds to dsDNA, and dsRNA of ssDNA-ssRNA duplex. The differential reflectivity measurement will allow measurement of reflectivity changes well below 1%, more typically below 0.1%. The measurement of small changes in reflectivity by the invented differential reflectometer will allow detection of redox reactions mediated by less than $10^{15}$ molecules, typically below $10^5$ molecules or 0.2 attomole. By scanning the laser beam over the microspots on each electrode, the level of probe-target specific binding will be obtained. By subjecting the electrode to different conditions, for example, different N with the same potential wave as mentioned above, the change in binding level as a function of N may be obtained for a given probe-target binding. Analysis of binding level as a function of N may lead to quantification of relative concentration of various target molecules.

BRIEF DESCRIPTION OF THE DRAWINGS

The accompanying drawings, which are incorporated in and constitute a part of this specification, illustrate one embodiment of the invention and together with the written description, serve to explain certain principles and features of the invention.

DETAILED DESCRIPTION OF PREFERRED EMBODIMENTS OF THE INVENTION

Reference will now be made in detail to various exemplary embodiments of this invention, examples of which are illustrated in the accompanying drawings. The following detailed description should not be understood as a limitation on the scope of this invention but should rather be considered as it is intended—to provide details on certain features and aspects of the invention. The chip design, the microarray fabrication process, the immobilization of the probe, conditions for specific probe-target binding, and the measurement approach will be significantly specific to illustrate the invention; however, it should not be construed as limiting. Those skilled in the art will appreciate variations in the design and process of the device to achieve the intended goal of obtaining data on specific binding as a function of binding condition to analyze for a relative amount of more than one target sequence in the solution by electrochemically regulating binding in the presence of a redox ion and electrochemically measuring probe-target binding by differential reflectivity. The chip device with more than one electrode patterned with microarray of probes, with combined concepts of electrochemical binding or EFIB and electrochemical differential reflectivity or SEED, constitutes the invention.

The details below include examples to demonstrate the translation of the principles of the device to practice the invention. The illustrations below exemplify some designs of the device to obtain data on specific binding as a function of binding by electrochemical methods. The specific design considered will underscore the concept of the invention to practice the regulation of binding kinetics that is mediated by a redox ion and measure the level of binding by differential reflectivity.

Figure 1A:
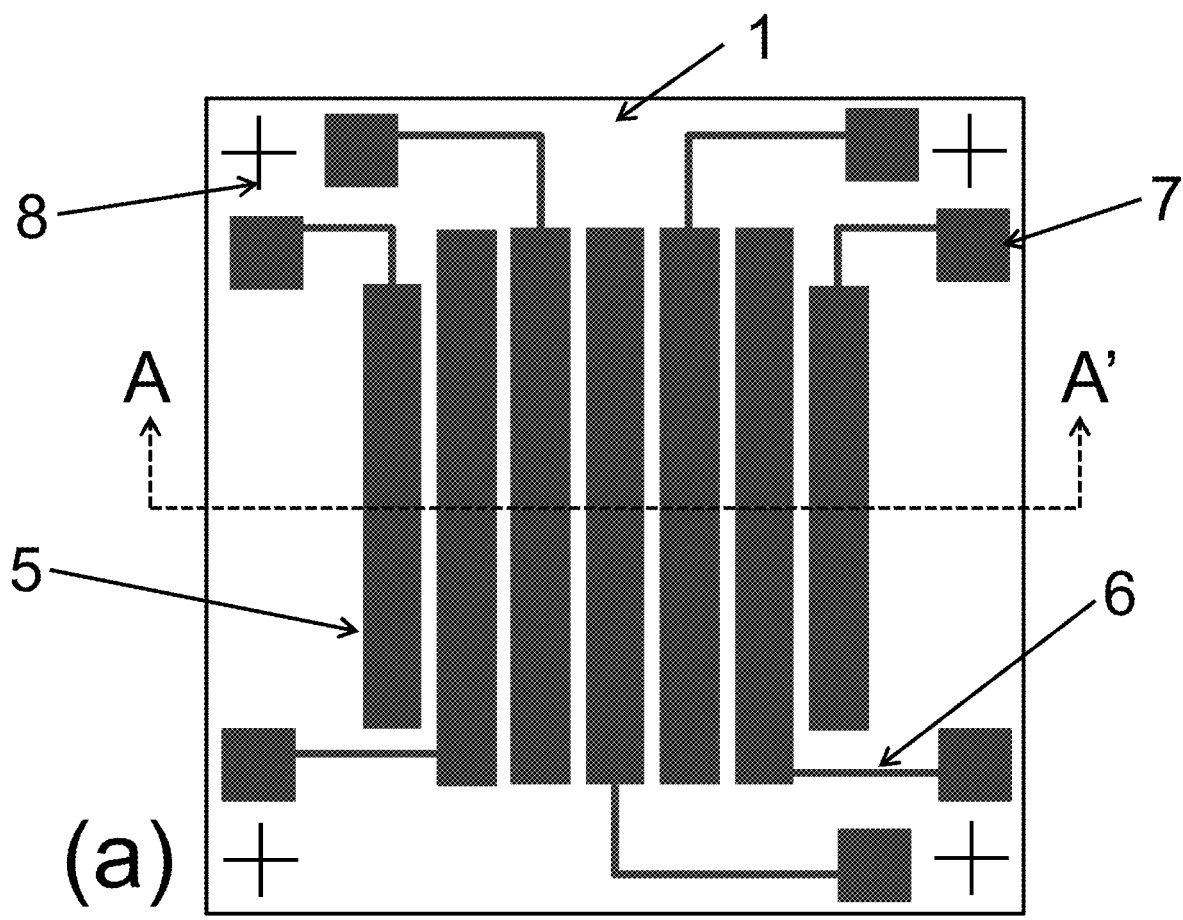
FIGS. 1a and 1b: Schematics of a typical chip with circuit lines for interconnection to electronics for power and signal.
Figure 1B:
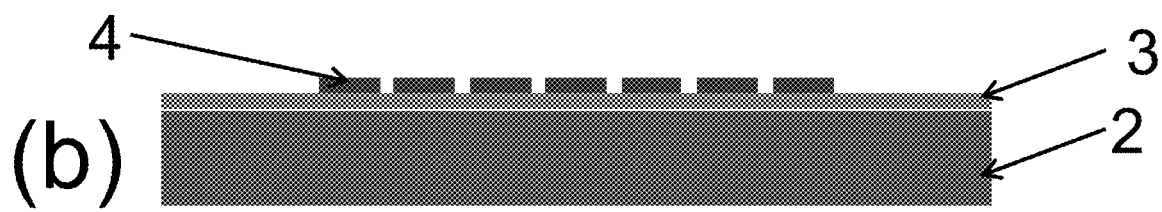

To demonstrate the concept of the invention, a simple device is considered that is comprised of a chip (1) shown in a schematic (FIG. 1). The relevant structure of the chip for the invention is shown as the top view (FIG. 1(a)) and cross-sectional view about the A-A' section (FIG. 1(b)). The chip (1) is a substrate (2) with an insulator layer (3) to isolate the electrodes (4,5). In principle, the additional insulating layer (3) is not required if the substrate (2) is an insulator, such as glass. The patterned electrodes (4,5) have good adhesion to the substrate surface so that they can withstand the conditions of device processing and operation. The patterned electrodes (5) are connected to terminal pads (7) via an electrical circuit (6). In principle, the electrodes (5), circuit (6), and terminal pads (7) may be fabricated by standard Si technology using photolithography. The circuit lines (6) and terminal pads (7) are so designed that the active part of the chip, i.e., part of the electrodes, may be in contact with fluid for electrochemical operations, while the lines (6) and the pads (7) are outside the fluid chamber to provide connectivity to electronics. The design of the chip is not unique. For example, those skilled in the art will appreciate several other designs are possible. For example, a multilayer design may be possible where electrodes, part of the circuit lines, and terminal pads may be on a different insulator layer that is hermetically sealed so that only the exposed area of the electrode is in contact with liquid for electrochemical operation. Such multilayer structures are well known in the art pertaining to Si-technology-based devices.

Figures 2A, 2B, 2C:
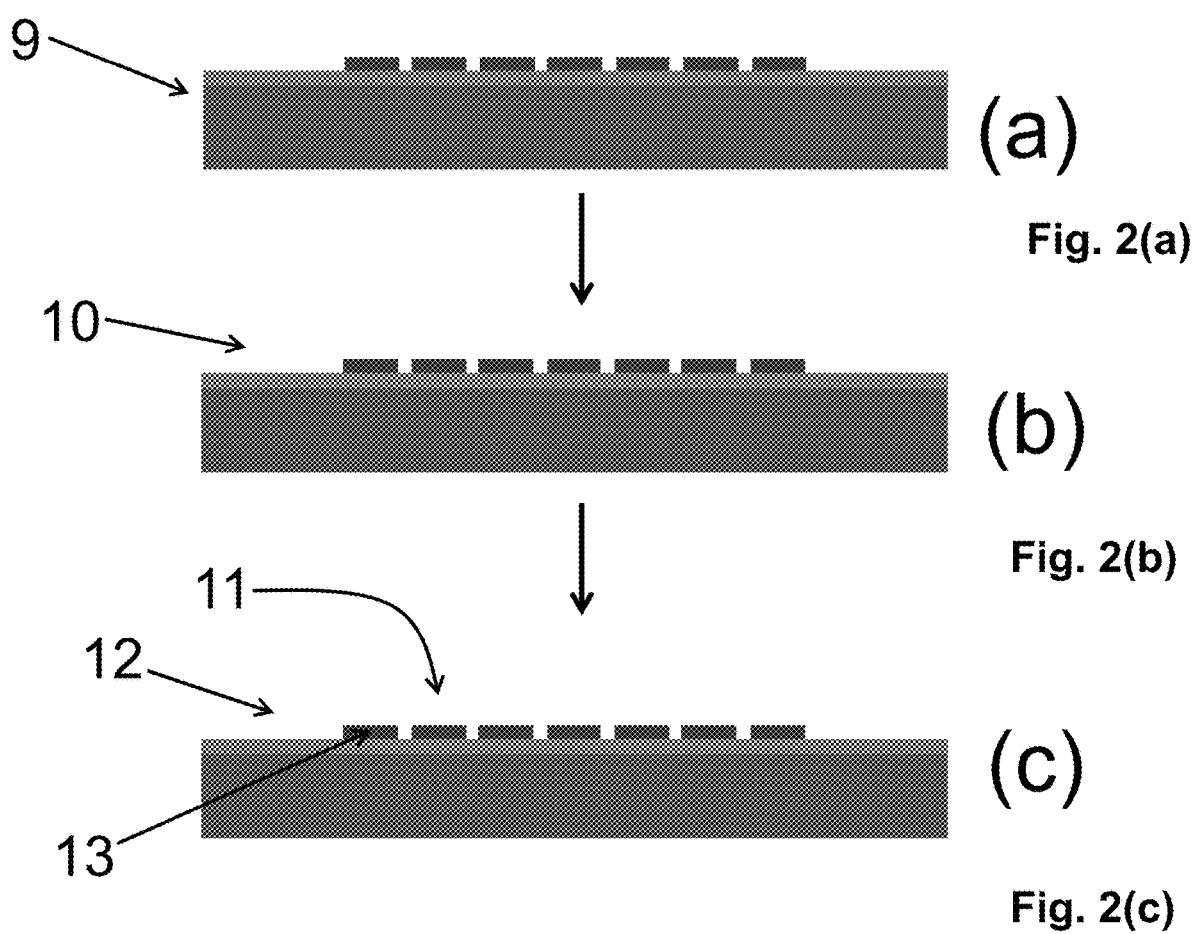
FIGS. 2a, 2b, 2c and 2d: Schematics of a typical photolithography process to fabricate an array of microspots on each electrode on the chip.
Figure 2D:
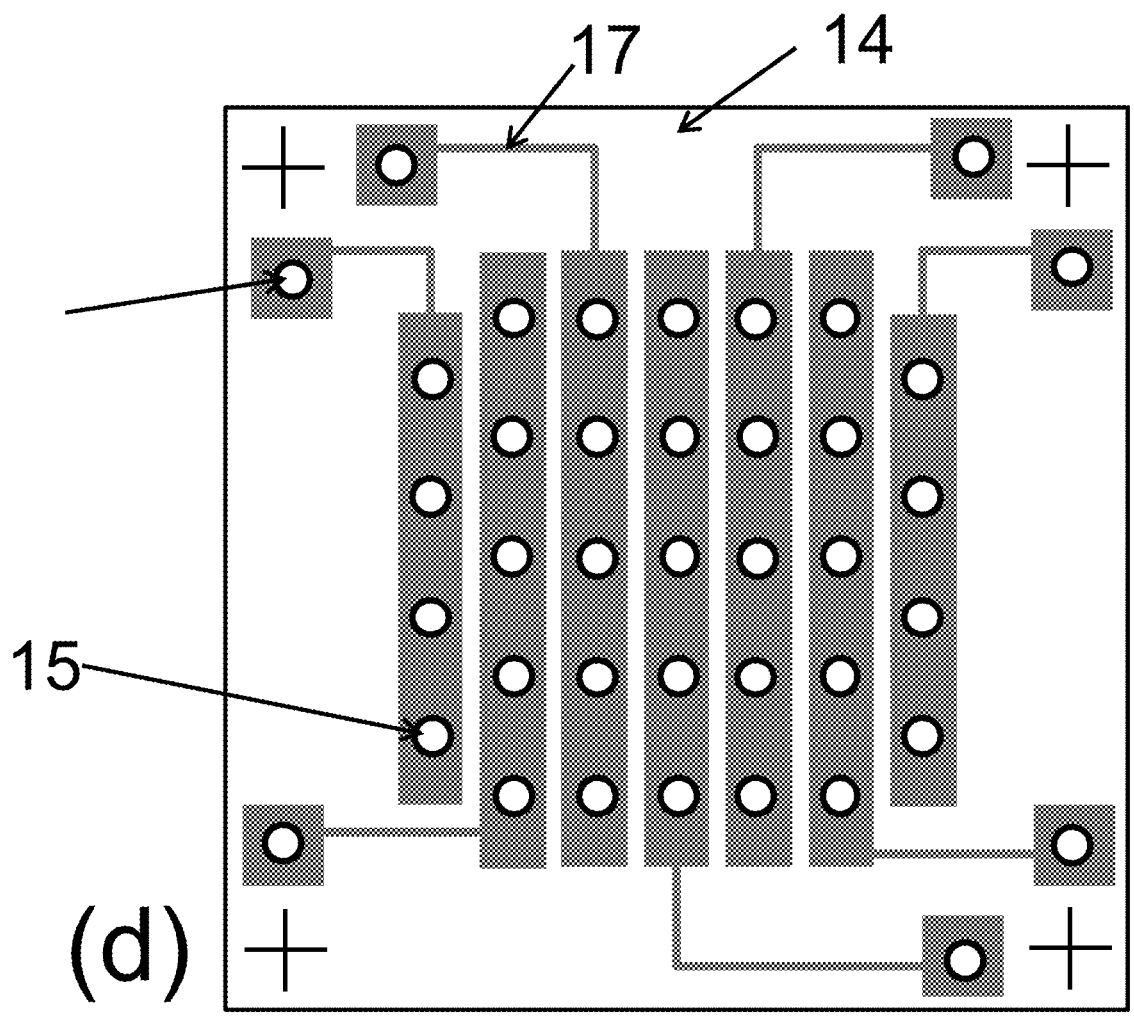

The fabrication of regions to immobilize microspots using photolithography is described next. The chip (9) shown in FIG. 1 and FIG. 2(a) is coated with a photoresist (10) (FIG. 2(b)). The resultant structure is exposed through an appropriate mask to selectively expose the area to be patterned and followed by a development process to form etched holes (11) in photoresist (12). Those skilled in the art appreciate that the design of the mask for photoactivation of the photoresist (10,12) will depend on if the said photoresist is positive or negative. The pattern on the photoresist (10,12) is aligned with the underlying electrode (13) using alignment markers (8) (see FIG. 1(a)), a standard practice. After developing the exposed photoresist, the electrode (13,4,5) is exposed. To ensure that the exposed electrode is devoid of any residuals from the photoresist, the chip may be cleaned using standard processes, such as wet processing using a solvent or a dry process using a reactive plasma gas. The resultant chip (14, 1) is coated with photoresist with etched holes (15) and (16) on electrodes and terminal pads, respectively, while the circuit lines (17) are protected by the photoresist. Only the exposed area on the electrodes may be exposed to liquid. The patterns of each etched hole on the electrodes (15) is considered as a microspot for immobilization (FIG. 2(d)). Those skilled in the art will appreciate that the nature and design of the pattern will depend on the type of array required for the application.

Figure 3A:
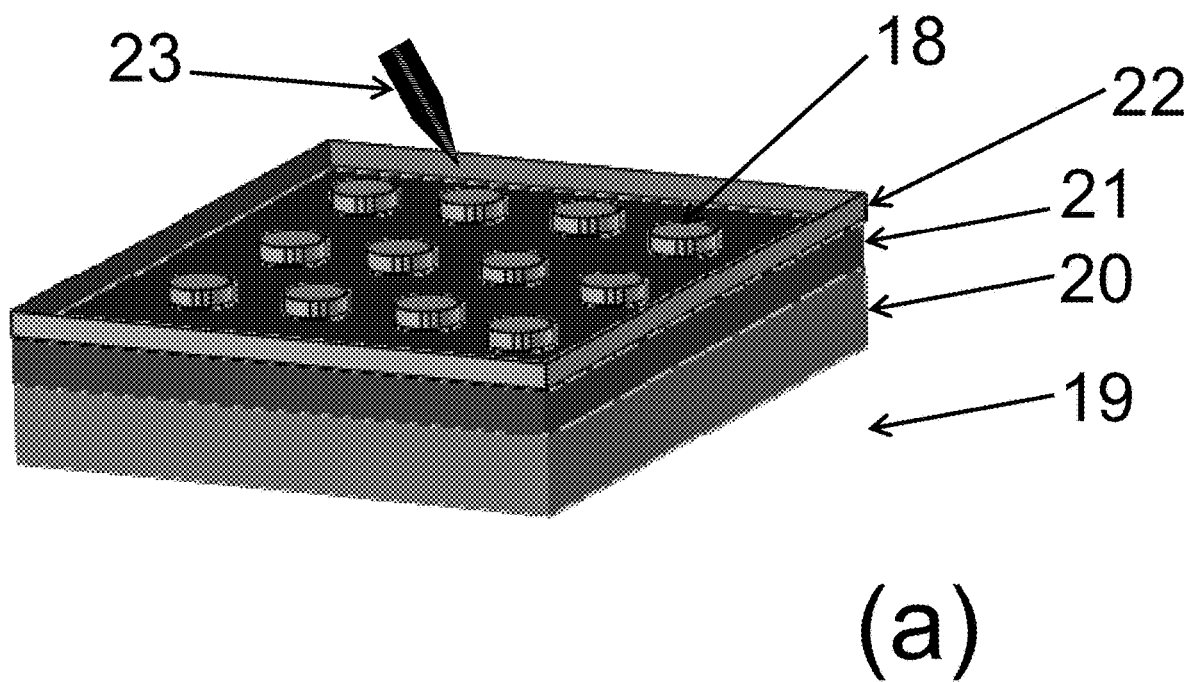
FIGS. 3a, 3b and 3c: Schematics of a typical spotting process to immobilize probe molecules on each microspot independently.
Figure 3B:
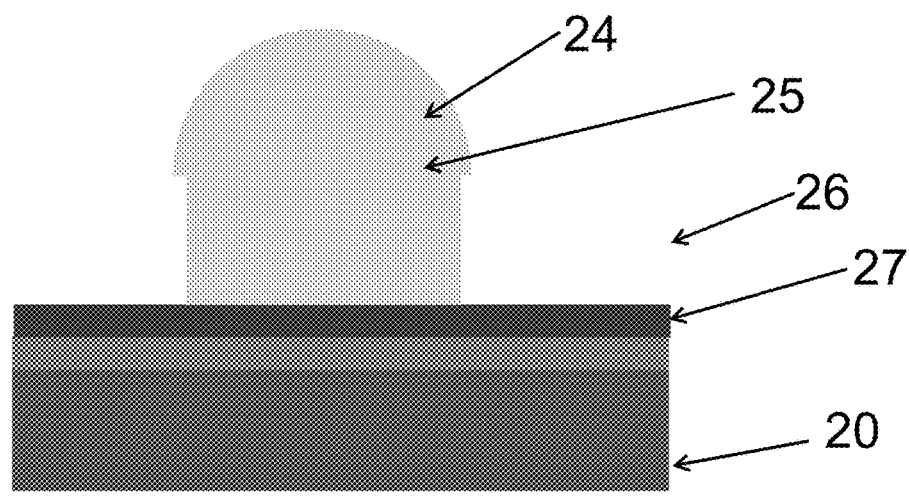

The process to immobilize probe molecules on microspots is described. To illustrate the probe molecule immobilization, an array of microspots (18) made by the photolithography process, i.e., (15) in FIG. 2, is considered (FIG. 3(a)). Only a portion of the multilayer structure of the chip is shown with the substrate (19), insulator layer (20), electrode (21,5), photoresist (22,10), and the etched holes (18,15) that expose the underlying electrode (21,5). The solution of probe molecules is dispensed on each etched hole (18) using a dispenser (23). The dispenser may be, for example, a micropipette tip or a capillary tip. The dispensed drop of target solution (24) on the hole (25,15) in photoresist (26,10) may be confined by surface tension (FIG. 3(b)). Those skilled in the art will appreciate that such a confinement is possible by making the photoresist hydrophobic. In one simple example, the electrode (27) in contact with the probe solution (24) may be Au or Pt; and the probe molecule has a thio-terminal group that will bind to the electrode forming a strong Au—S or Au—Pt bond. After subsequent washing to remove excess chemicals, the result is tethered probe molecules (28) attached to the electrode at one end (29,5) (FIG. 3(c)), that may subsequently bind to target molecules. Typically, the probe sequence (28) will be different for various holes (30, 15). Those skilled in the art will appreciate that depending on the chemistry of immobilization, the electrode surface may be modified before dispensing the solution of the probe molecules. The simple example using a Au or Pt electrode to tether the probe molecules without any modification of the electrode surface is well described in the literature. Several immobilization processes are documented in the literature which, for the invention, may constitute standard methods practiced in the art. There are several strategies to immobilize the probe on a surface; and they are well reviewed in the literature, for example, using thio-terminated probes, conducting polymers, proteins, and vitamins. Furthermore, those skilled in the art will appreciate that there are other methods to fabricate microarrays on the electrodes (5, FIG. 1(a)). For example, instead of using photolithography (FIG. 2), it is possible to make the microspots by soft lithography where features of poly(dimethyl siloxane) may be patterned on the Au electrode by stamping followed by $NH_3$ plasma to activate amine groups to tether probe molecules by dispensing the probe solution by similar method in FIG. 3(a) using a micropipette or a capillary pin. The second alternative is described to simply demonstrate that the fabrication of the microarray of probe molecules on the electrode is not limited to the invention as long as localized immobilization of different probe sequences on an electrode to form an array of microspots is possible. There are multiple methods described in the literature, and there may be methods developed and published in the future.

The chip with an array of immobilized probes on different electrodes may be exposed to the solution of targets obtained from the biospecimen. The method of electrochemical binding is based on a submitted patent application on a device to electrochemically enhance probe-target binding by EFIB Specifically, the invention expands on the said submitted application to regulate the binding from a low amount of binding to a high amount of binding. The specific application described is to illustrate one example to translate the invention to practice without limiting the overall teaching of the invention.

Figure 3C:
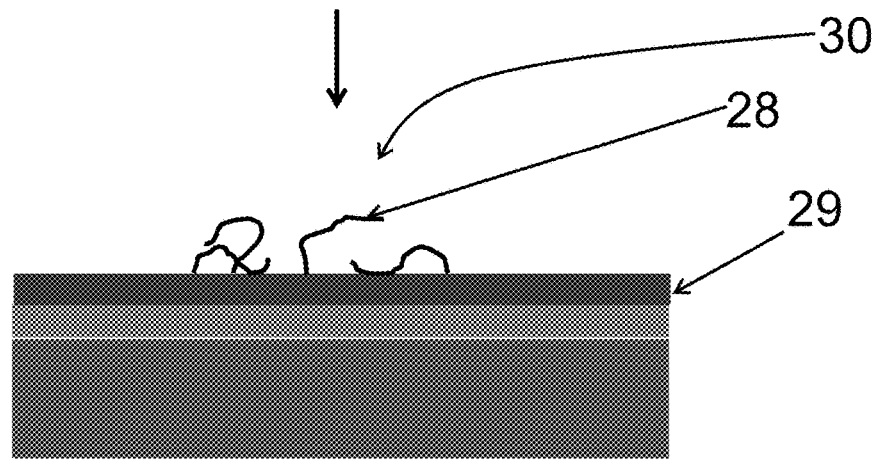
Figure 4:
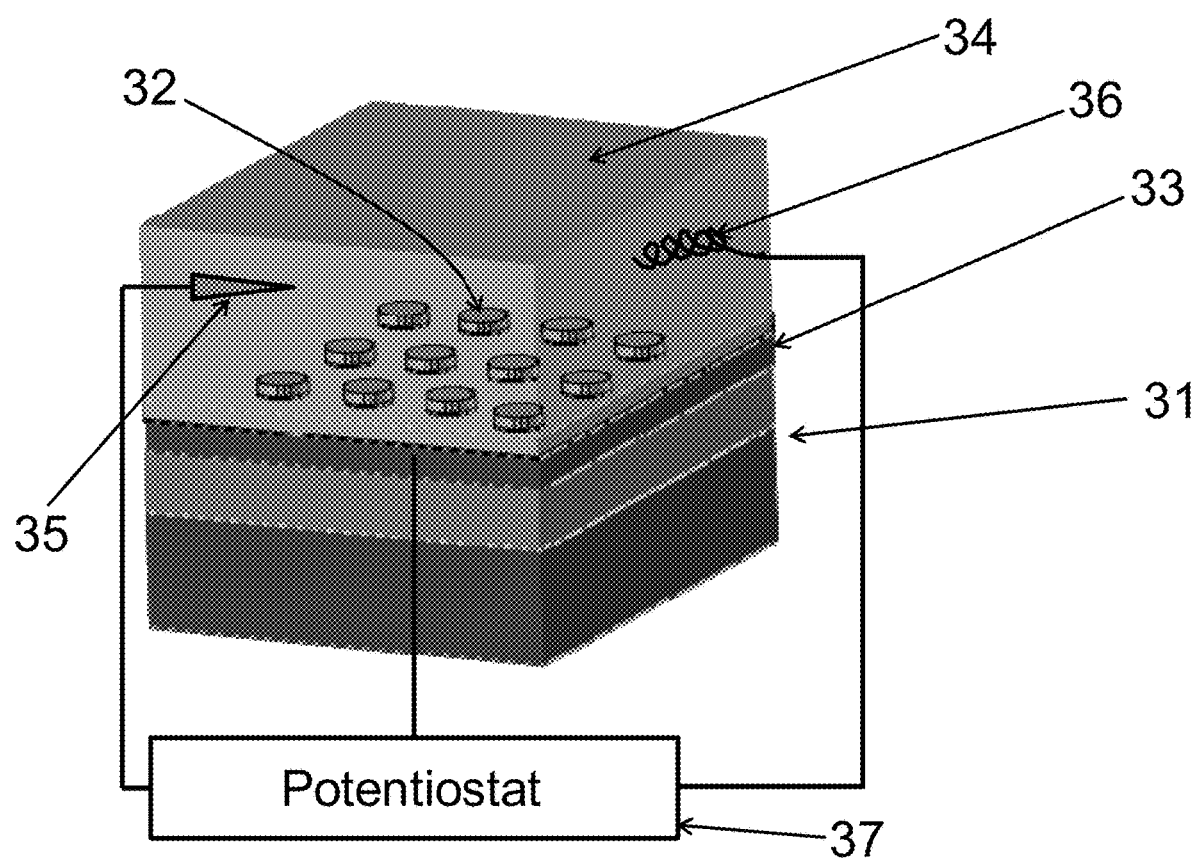
FIG. 4: Schematic of a typical process using a potentiostat to electrochemically regulate the amount of probe-target binding on an array of each electrode independently.

To demonstrate the concept of the invention, the binding process is illustrated by considering a portion of the chip with microspots (FIG. 3, (18)-(22)) with each microspot with immobilized probe molecules (FIG. 3(c), (28)). The said multilayer chip (31) (and (14)) with microspots (32) that each has immobilized with a probe molecule on the underlying exposed electrode (33) is subjected to a potential, E', applied between the solution (34) and the electrode (33) (FIG. 4). The potential, E', is applied using, for example, the well-known three-electrode arrangement. The potential, E', is applied between the reference electrode (RE) (35) and the working electrode (WE) (33); and the redox current, I, is measured between the counter electrode (CE) (36) and the WE (33). The oscillatory potential, E', and the current, I, are applied and measured, respectively, by a potentiostat (37). A specific potential, E', applied via the potentiostat may be a triangular wave at a frequency, w, in the range of 1 mili-Hz to 1 mega-Hz, preferably in 100 mili-Hz to 100-Hz. The redox ion use to regulate the binding process may be an $E°$ >0, for example, $[Fe(CN)_6]^{4-}$. The range of the oscillatory cycle may be from −0.7 to 1 V, preferably, −0.5 to 0.8 V. Importantly, the range of oscillatory cycle adequately covers the redox potential, $E°$.

The specific binding of target molecules to probe molecules in each microspot on the chip over all the electrodes will be measured by scanning a laser beam to measure differential reflectivity. The instrument to measure differential reflectivity or SEED is based on U.S. Pat. No. 7,826,060 Specifically, the invention expands on the said submitted application to determine the relative concentration of target molecules by obtaining the relative level of binding on each microspot of the array on all of the electrodes on the chip that are subjected to different binding conditions. The specific optical setup described is to illustrate one example to translate the invention to practice without limiting the overall teaching of the invention.

Figure 5:
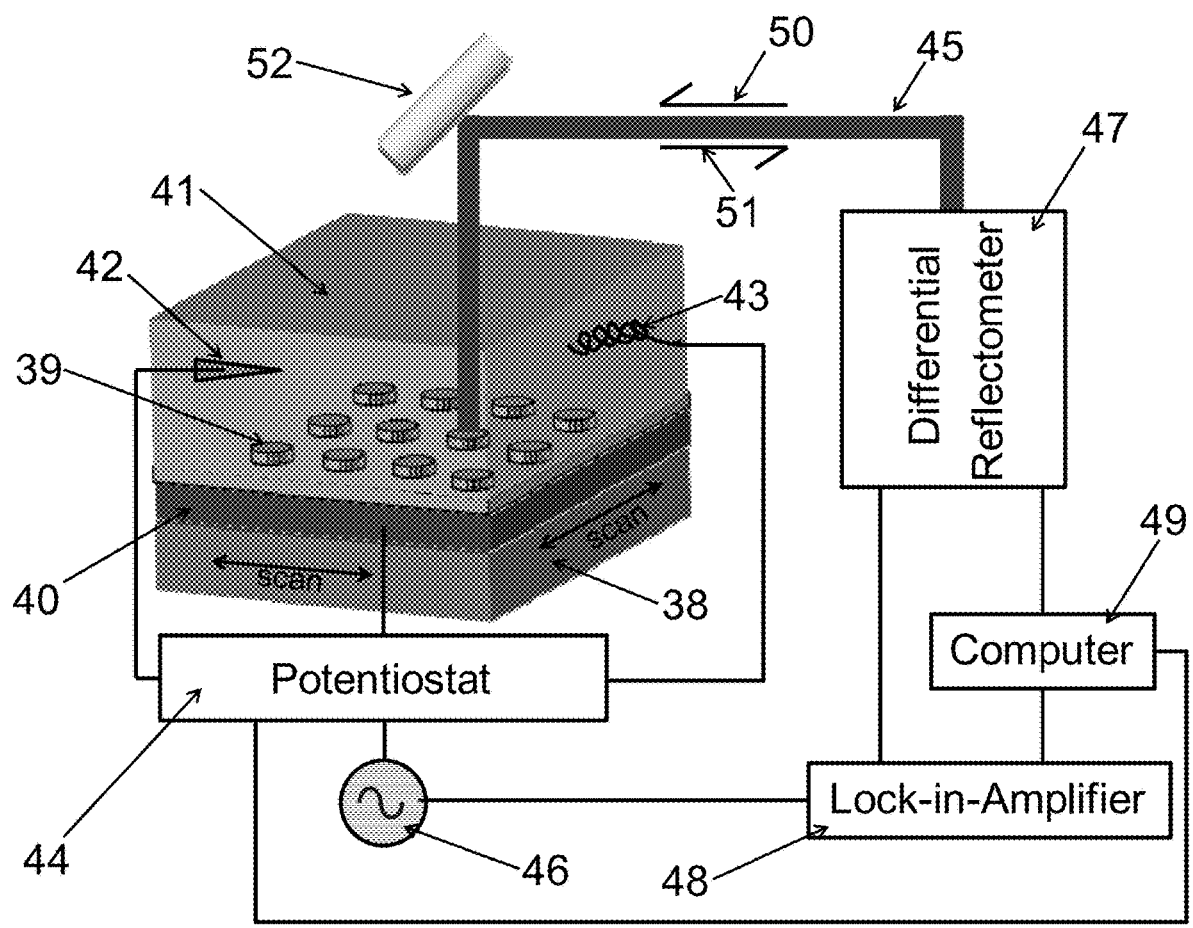
FIG. 5: Schematic of the device to measure reflectivity of a laser beam on each microspot by scanning the chip.

To demonstrate the concept of the invention to measure binding, it is illustrated by considering a portion of the chip with microspots (see FIG. 3, (18)-(22)) where each microspot has immobilized probe molecules (see FIG. 3(c), (28)). The said multilayer chip (31) (and (14)) with microspots (39) each of which has an immobilized probe molecule on the underlying exposed electrode (40) is subjected to a potential, E, applied between the solution (41) and the electrode (40) (FIG. 5). In this drawing, without any loss in generality, the substrate of the chip is only one insulator layer. The potential, E, is applied using, for example, the well-known three electrode arrangement. The potential, E, is applied between the RE (42) and the WE (40); and the redox current, I, is measured between the CE (43) and the WE (40). The oscillatory potential, E, and the current, I, are applied and measured, respectively, by a potentiostat (44). A specific potential, E, applied via the potentiostat may be a triangular wave at a frequency, w', in the range of 1 mili-Hz to 1 mega-Hz, preferably in 10 mili-Hz to 100-Hz. To measure the binding, a redox system, such as MB with $[Fe(CN)_6]^{4-}$ as a mediator, may be used. MB specifically binds to the duplex on the site of specific binding.[10] The range of the oscillatory cycle depends on the redox ion system; for example, for MB with $[Fe(CN)_6]^{4-}$, — the range may be −0.6 to 0 V.

To measure the differential reflectivity of the laser beam (45), an auxiliary potential may be applied via the potentiostat (44) using an extra power supply (46). The role of the auxiliary potential at frequency, $\omega"$, is to oscillate the reflectivity of the electrode (40) by oscillating the ions in the interface of the electrode (40) and solution (41) at the same frequency, $\omega"$. The auxiliary potential at frequency $\omega"$ is identical to the AC potential first mentioned earlier in the section, "The Field of Invention". The amplitude of oscillation in the reflectivity is measured by the differential reflectometer (47) with the output amplified in a lock-in amplifier (48) referenced at $\omega"$ by the power supply (46). The data is acquired and analyzed by the computer (49) that interfaces with the detector in the differential reflectometer (47), the lock-in amplifier (48), the potentiostat (44), and the motors to scan the chip (38). The detector in the differential reflectometer (47) is to measure the incident intensity of the laser, $I_O$, which is an important parameter to calculate the reflectivity. The details of the differential reflectometer are described in the SEED patent The differential reflectivity, R, defined as the amplitude of the reflectivity at $\omega"$ on each microspot, is measured on all of the microspots on the chip. Typically, for a given probe-target specific binding, R as a function of N may be measured to estimate the concentration of the target in the solution.

The mode of measurement is by no means unique. For example, based on the SEED patent, the incident (50) and reflected (51) beam may not retrace because the incident laser beam on the sample may be at an angle regulated by the steering mirror (52). For the beam at an angle would require extra optics, as described in the invention on differential reflectometer One approach to estimate an unknown concentration of targets of known sequence obtained from a biospecimen is by calibrating the differential reflectometer for a given target sequence using synthetic oligomers.

Example: Calibration

The probe is ssDNA corresponding to microRNA-155 (miR-155). Specifically, the sequence is 5'-HS-$(CH_2)_6$-AAA TTA ATG CTA ATC GTG ATA GGG GT-3'. Similarly, the second probe corresponds to miR-21 with a thio-linkage at the 5'-end as the miR-155 probe. The chip has six electrodes, each having seven microspots. As defined above, K=7. The 50 μm microspots are patterned by photolithography using SU8 as photoresist. MiR-155 and miR-21 probes are immobilized on five and two of the seven microspots, respectively, on each electrode. The electrode is Au. The immobilization is via the Au—S linkage.

The binding is performed in solution containing 10 fM of target complementary to a miR-155 probe in a 100 mM phosphate buffer and 50 mM of $K_4[Fe(CN)_6]$. The $[Fe(CN)_6]^{4-}$ is the redox ion that promotes and regulates binding with $E°$ ~0.22 V. The binding is conducted by ramping the potential, $E'$, from ~400 to 300 mV.

Figure 6:
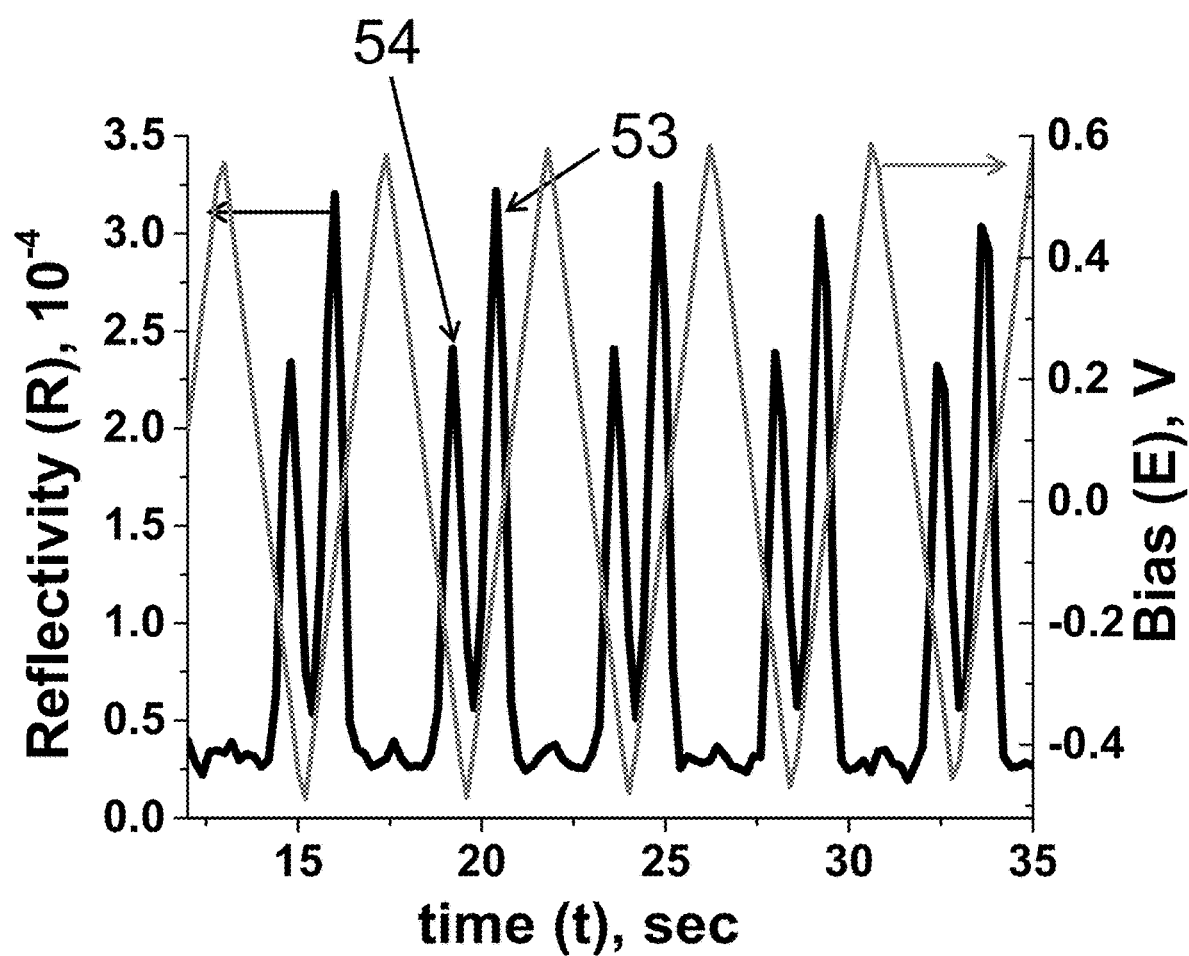
FIG. 6: A typical scan showing differential reflectivity (R) from a microspot with specific binding as the oscillatory "V-shaped" ramp-potential is applied to the chip.
Figure 7:
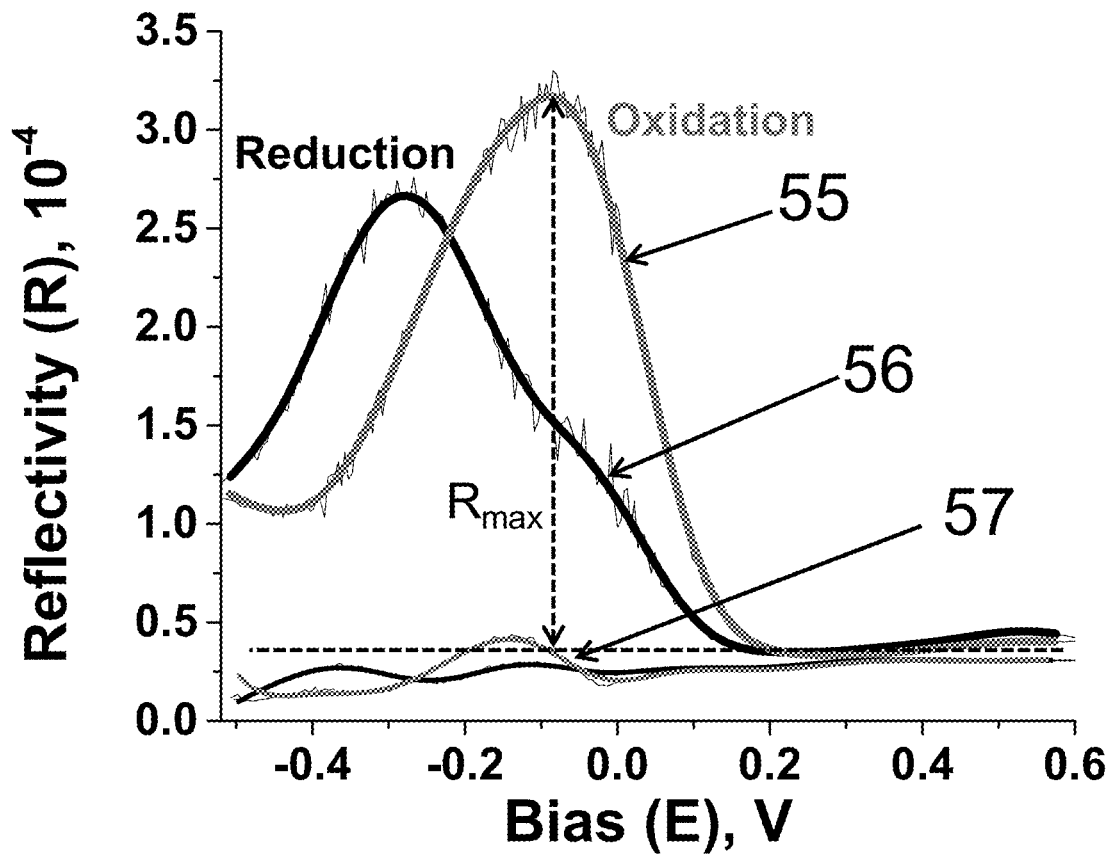
FIG. 7: The redox of MB from two microspots with specific and nonspecific binding on the same electrode subjected to identical binding conditions.

After vigorously washing the chip in RNAase-free water, differential reflectivity measurements are performed with a ramp cycle from −500 to 600 mV and the probe potential at an amplitude of 100 mV and frequency, $\omega$=2 KHz. The differential reflectivity measurement is performed in 100 mM phosphate buffer and 10 μM of MB. For N=32 binding cycles of $E'$, typical data on a microspot with specific binding shows the modulation R at $\omega''$ (left-axis) as the ramp-potential oscillates (right-axis) (FIG. 6). The MB oxidation peak (53) during up-ramp and reduction peak (54) during down-ramp are reasonably reproducible from cycle to cycle. The average and cumulative response of E versus R shows the average oxidation and reduction of MB with the cumulative noise over about 25 scans (FIG. 7). $R_{max}$ is the maximum differential reflectivity for the oxidation peak (55).

Figure 8:
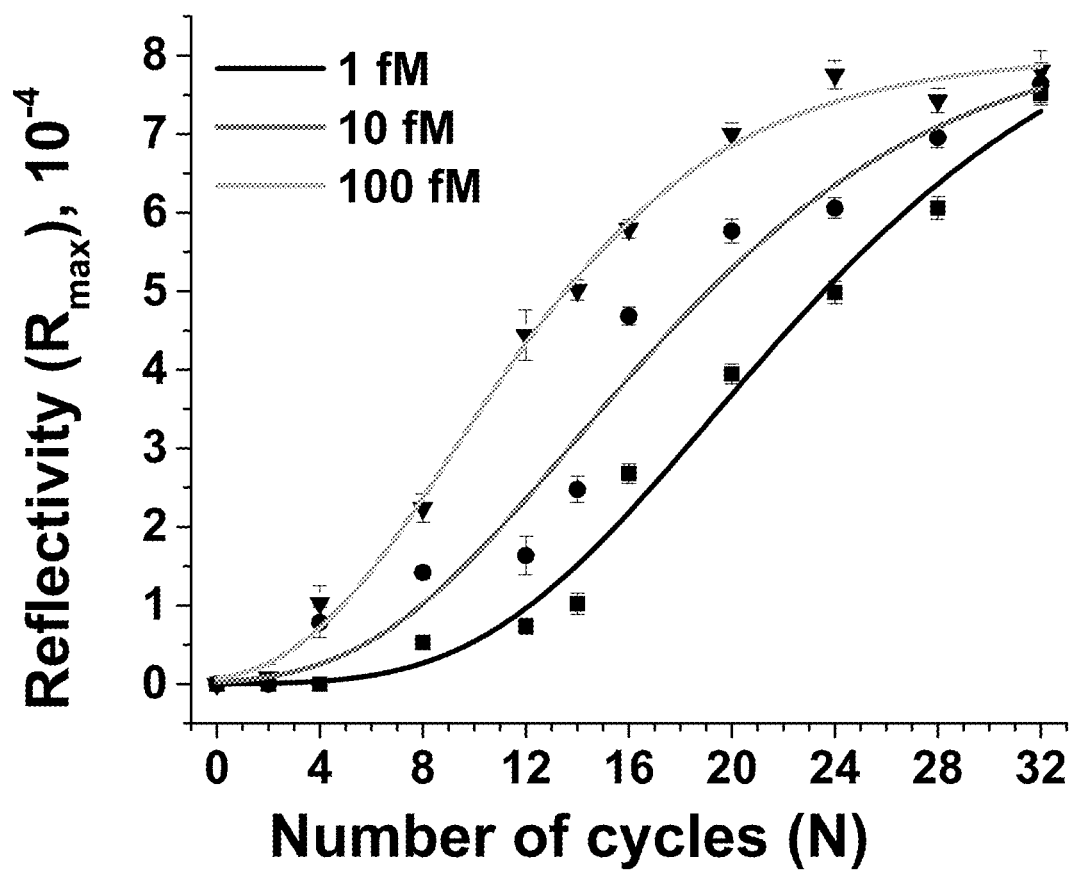
FIG. 8: Change in $R_{max}$ as a function of N comparing three different target concentrations.
Figure 9:
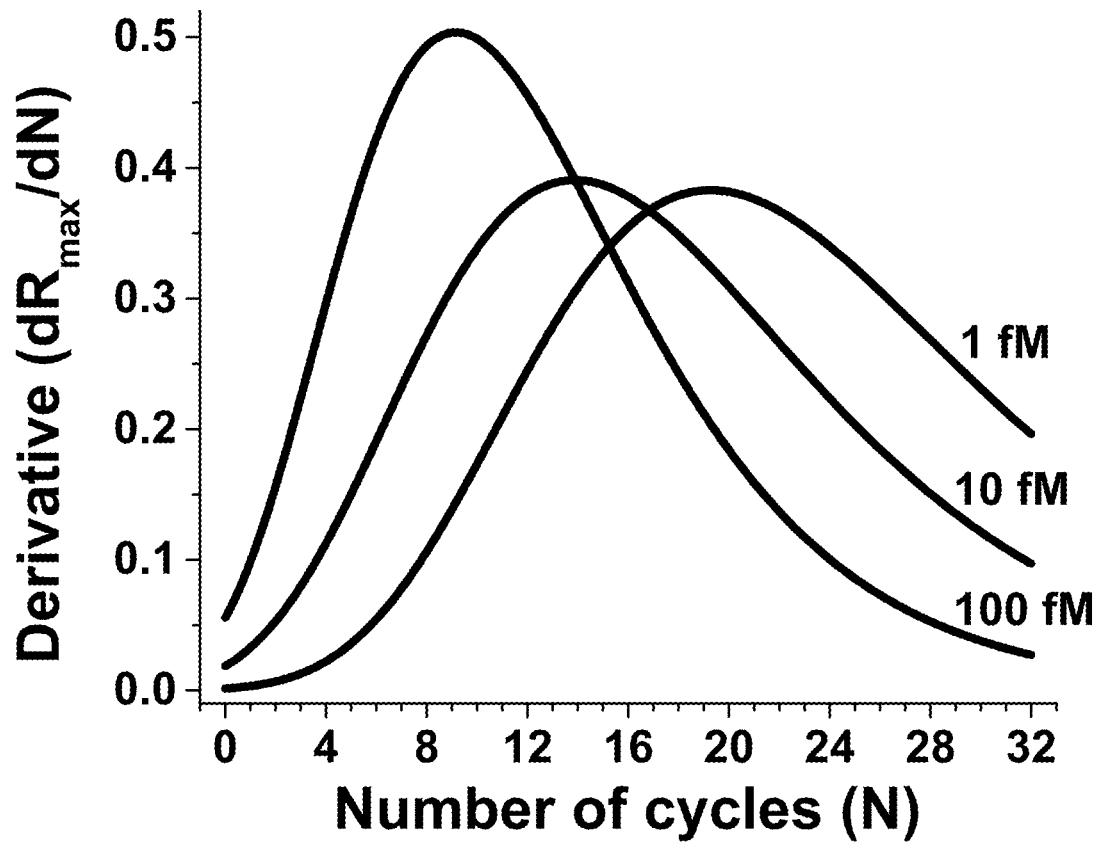
FIG. 9: Derivative of $R_{max}$ with respect to N as a function of N.
Figure 10:
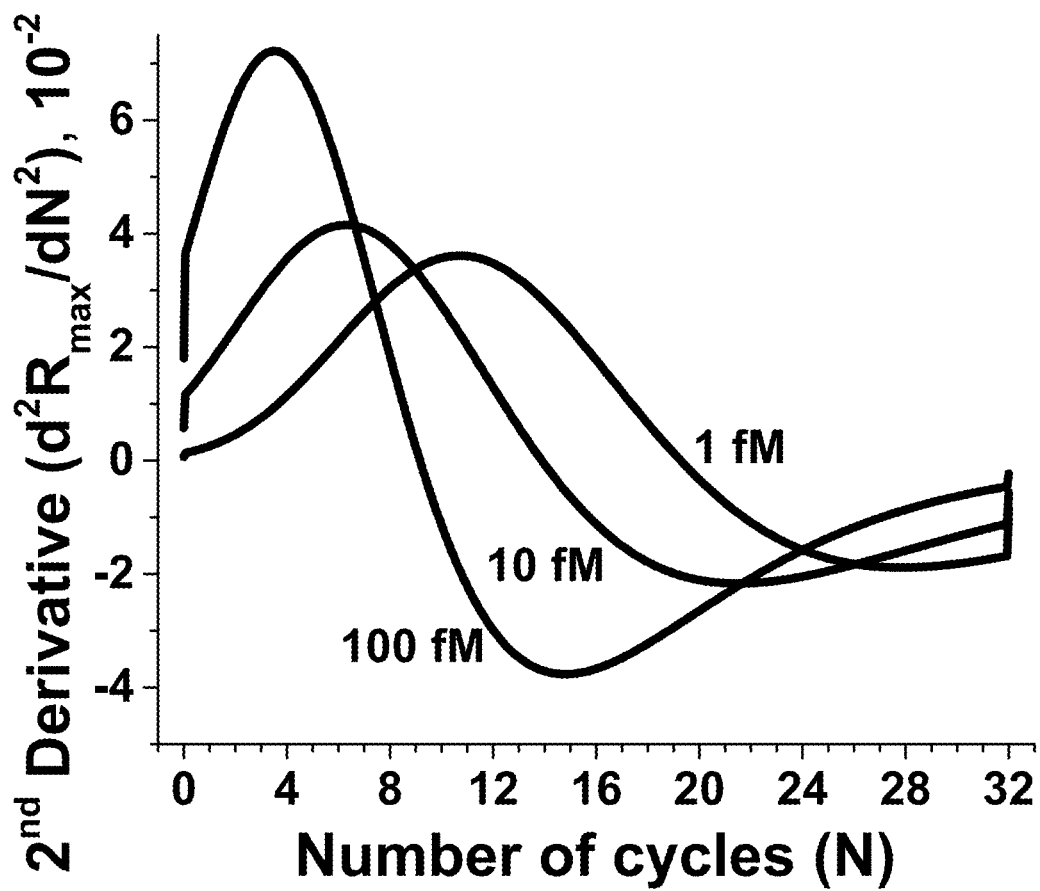
FIG. 10: Second derivative of $R_{max}$ with respect to N as a function of N.

Based on six chips, over 10 electrodes, $R_{max}$, as a function of N, are measured for three target concentrations (FIG. 8). A sigmoidal curve is fit to the data using nonlinear regression analysis. The subsequent analysis using first and second derivatives is on the sigmoidal curve fit to the data. For low concentration, $R_{max}$, at low N is zero, while for high concentration, $R_{max}$, saturates at large N. There is a clear inflection point in the sigmoidal curve as clearly observed as a maxim in the derivative (FIG. 9). The inflection point, at N=$N_P$, is measured in the second derivative curve, as shown for 1 fM target concentration. The inflection point, as expected, decreases as target concentration increases from 0.1 fM to 1000 fm (or 1 picomolar). The linear curve on the semi-log plot may serve as a calibration curve for unknown target concentration.

Figure 12:
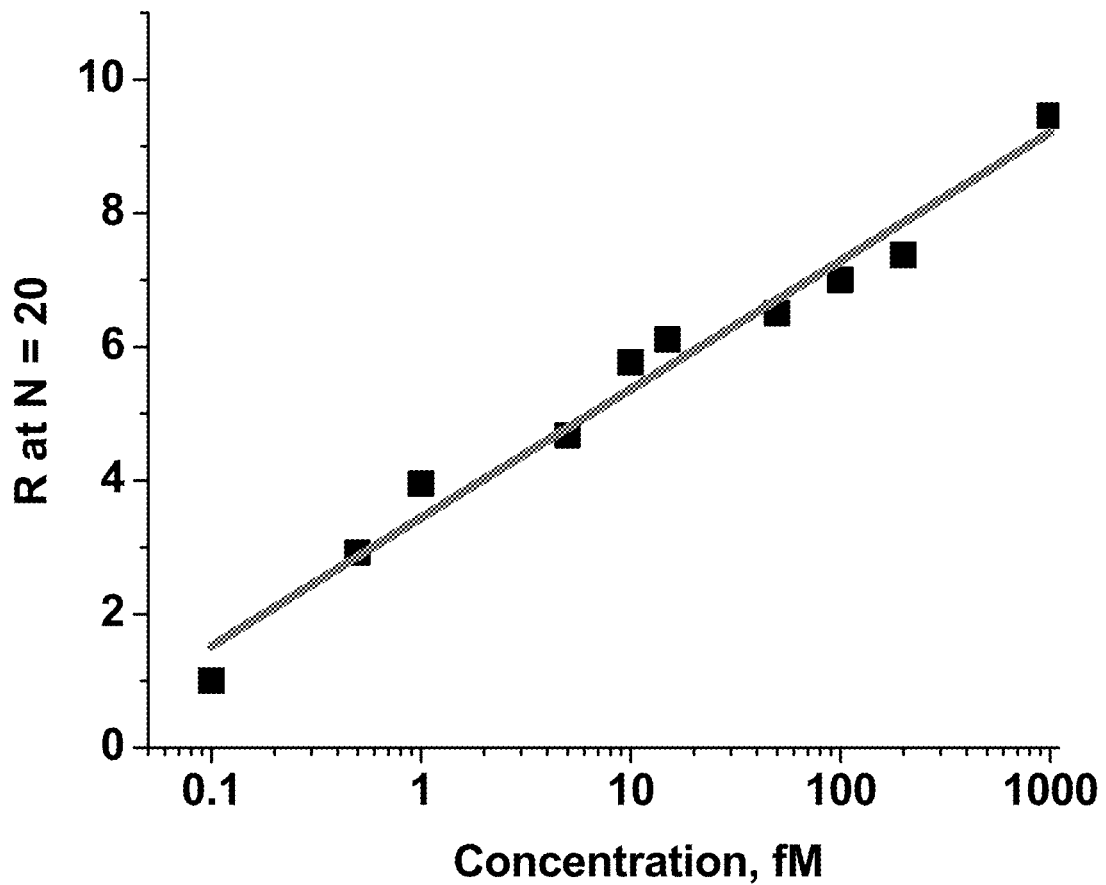
FIG. 12: The reflectivity, $R_{max}$ as a function of target concentration for N=20.

An alternative approach to determine the target concentration would be to plot $R_{max}$ at a fixed N as a function of concentration (FIG. 12). By determining the $R_{max}$ at the same N for a sample with unknown amount of target, the calibration curve (FIG. 12) will allow determination of the target concentration of the unknown sample.

Figure 11:
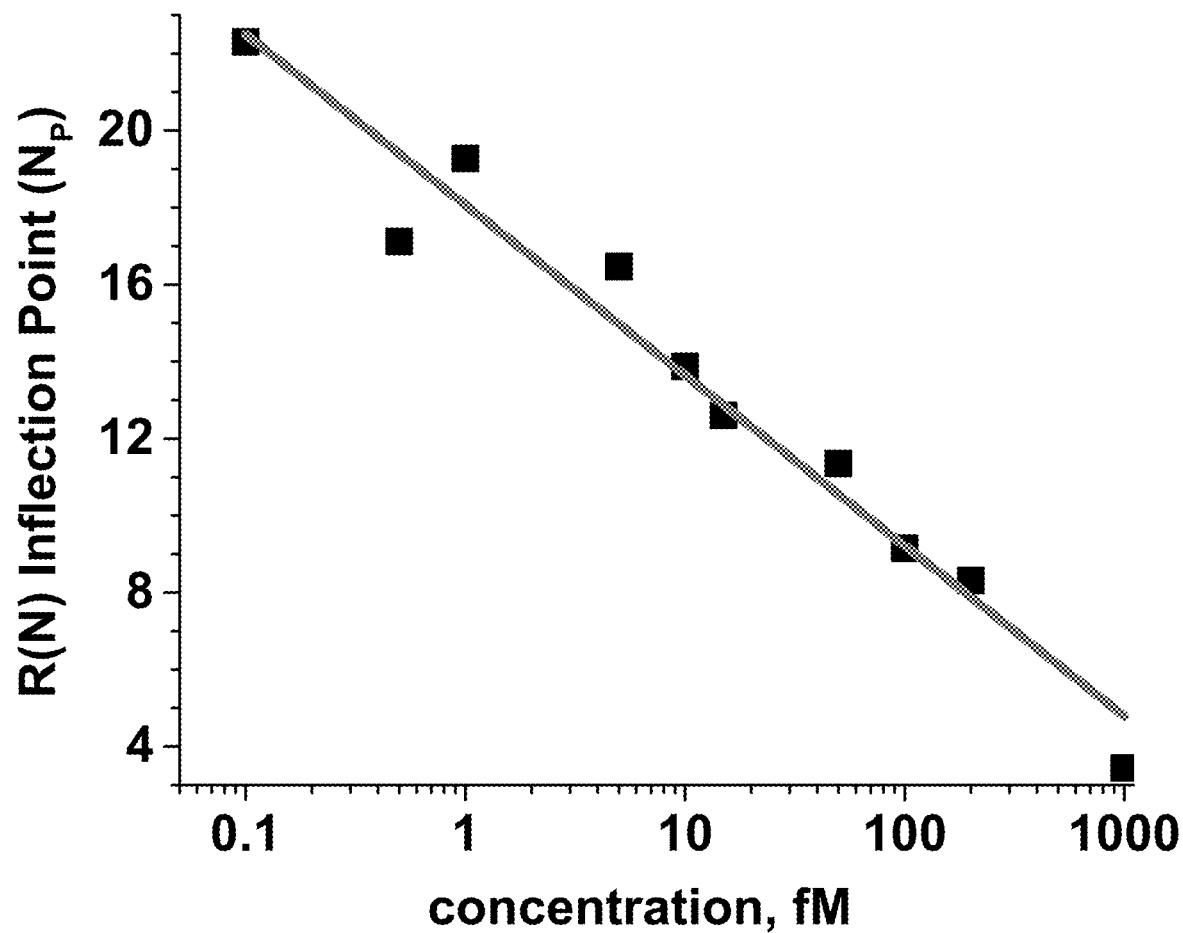
FIG. 11: The inflection point, $N_P$, as a function of target concentration.

Those skilled in the art will appreciate that because the hydrogen bonding strength of the various base pairs is significantly different, the calibration curve (FIG. 11 and FIG. 12) may depend on the sequence and length of the target, and the relative location of the probe target binding. As a result, calibration curve for each target-probe pair that may be of interest may have to be obtained using synthetic probe and target molecules, as performed in the above example. Once the calibration in a given buffer solution is obtained, those skilled in the art will appreciate that analysis for concentration of target from biosamples will be possible.

The example illustrates that the approach demonstrated can be used to measure unknown target concentration in the fM range from a biospecimen. As the volume of the sample during binding was 0.5 mL, the method with sensitivity of 0.1 fM corresponds to the ability to measure $3\times10^4$ target copies from a biospecimen.

Example: Liquid Biopsy

This example illustrates a particular application of method to obtain relative concentration of a mixture of target molecules of known sequence of ssRNA or ssDNA obtained from a biological specimen, such as blood, urine, sweat, saliva, and stool. The chip to quantify relative concentration of more than one sequences of target will comprise of immobilizing a microarray of complimentary probe for each of the targets on the electrodes. The relative concentration of each sequence can be quantified using their respective calibration curve. It will be obvious to those skilled in the art that the calibration curve for each target may be obtained using a single target sequence target, or additional sequences may be mixed that would serve as a background that will not specifically bind to the probe but may hinder the specific probe-target binding. The analysis to obtain relative concentration of know nucleic acids in the above said biological specimen is generally called liquid biopsy.

By applying different EFIB conditions on the respective electrodes on the chip, different level of binding may be obtained on each electrode. For array with identical probes on each electrode, the level of binding of the target to the complimentary probe can be regulated. For example, the sensitivity may be enhanced by increasing the EFIB process, for example, by increasing the number of cycles, N. Furthermore, on a different electrode of the same chip, the EFIB process can be reduced to measure targets with high concentration without saturating the signal. Thus, by regulating the EFIB process among electrodes, and inserting fresh solution from the same stock of solution, both high sensitivity and large dynamic range may be obtained. Furthermore, an electrode with no EFIB may be included to obtain base-line SEED signal corresponding to no binding.

Example: mRNA Analysis

To obtain transcriptome information, typically, messenger RNA (mRNA) is extracted from biospecimen, such as, blood, tissue, or cell culture using well known molecular biology processes well known in the art. Usually, the amount of mRNA, referred to as expression of the gene, is measured by randomly fragmenting the large mRNA in short pieces followed by their amplification using a PCR. The amplification is necessary because the number of copies is too small to measure. Owing to the high sensitivity of the method described here, no fragmentation or PCR amplification will be needed to analyze the expression of the gene.

First, to practice the method described here, the mRNA may be directly extracted from the biospecimen using immuno-extraction also well known in the art. For immuno-extraction, for example, commercially available magnetic beads with ssDNA with only T-base tethered to the surface is mixed with biospecimen suspended in a buffer. The beads are referred to as BEAD-T for simplicity. The RNA may be extracted from the biospecimen and suspended in the buffer or the biospecimen may simply be lyased and suspended in the buffer without and further extraction. The buffer may for example be phosphate buffer, a standard solution well know to experts in the art. The T-tails of the BEAD-T attaches to the A-tail of mRNA. By adding BEAD-T in excess it is ensured that almost all the mRNA is immunospecifically attached to the beads.

Second, as the sequence of the target mRNA is known, the mixture is then exposed to small target ssDNA that will bind to sites of the mRNA that are complimentary to the target sequence. The length of the target ssDNA complimentary to specific sequence segments (SSS) of each mRNA may be less than 500 nucleotides, preferably less than 100 nucleotides. The set of SSS to uniquely identify an mRNA of known sequence may be determined by standard bioinformatics analysis. The set of SSS for a specific mRNA of interest may have as few as one site to many, typically two to five sites in the set will uniquely identify the mRNA. The target ssDNA specific to SSS are in excess to ensure almost all the intended SSS segments for each mRNA is bound to the specific ssDNA target. The beads are separated from the excess ssDNA solution by a magnet using a standard method. The separated mRNA with ssDNA targets on the BEAD-T is digested by an RNAase enzyme, and the ssDNA targets are collected as supernatant and suspended in a buffer using a standard protocol.

Third, the ssDNA target is directly analyzed by SEED instrument (in FIG. 5) using a chip (14). The microspots (18) correspond to various probes complimentary to the ssDNA targets. It is understood that the number of microspots with probes are sufficient to address all the targets with appropriate statistics. The SEED analysis is performed to measure the relative copy number of each ssDNA target as described above to calculate the relative copy number of each mRNA.

In review in this invention, sequences of multiple ssDNA or ssRNA target molecules may be determined by binding them to an array of microspots of immobilized probe ssDNA, ssRNA or ssPNA molecules on a solid substrate with complimentary sequences that may be different on each spot. Typically, the method to determine binding is optical or electronic. The binding to all the microspots is concomitant under identical conditions. This method to determine the sequence and relative quantity of various targets is referred to as microarray chip technology.

A microarray chip on more than one electrode where the binding to each array on respective electrode is controlled from virtually no binding to significantly high binding and determining the level of binding on each spot of the array by spot-to-spot scanning of the laser beam. The binding is performed electrochemically by applying a cyclic potential between the electrode with the microarray of probes and the solution in presence of a redox ions. By controlling the number of cycles, frequency, and the range of potential applied on each electrode, the level of binding may be controlled on respective electrodes from no binding for no application of potential to significant binding due to potential application. The process to measure binding on each spot is by SEED. It can be done by other methods such as fluorescence or conventional electrochemistry. The process of binding is by EFIB. Binding without the auxiliary ion is also possible as long as it can be tuned.

On the same chip with multiple electrodes, different level of binding may be obtained on respective electrodes. For array with identical probes on each electrode, the level of binding of the target to the complimentary probe may be regulated by varying the EFIB condition. For example, the sensitivity may be enhanced by increasing the EFIB process, for example, by increasing the number of cycles. Furthermore, on a different electrode of the same chip, the EFIB process can be reduced to measure targets with high concentration without saturating the signal. Thus, by regulating the EFIB process among electrodes, and inserting fresh solution from the same stock of solution, both high sensitivity and large dynamic range may be obtained. Furthermore, an electrode with no EFIB may be included to obtain base-line SEED signal corresponding to no binding.

Target ssRNA and ssDNA sequence obtained from biospecimen using standard column extraction methods may be analyzed on a single chip. The relative concentrations of the different target sequences may range over a large dynamic concentration range. A dynamic range of at least five orders of magnitude may be measured on a single chip by proper optimization of the EFIB condition on different electrodes.

Usually to analyze the expression level in a cell the large molecule is fragmented by mechanical shearing. The fragmentation is random. Here, the mRNA may be analyzed without fragmenting the molecule. The process is described in the specs. The patentability is that the target ssDNA that is proportional to the mRNA copies can be directly analyzed on the chip because of the high sensitivity and large dynamic range. The high sensitivity and dynamic range, allows the avoidance of PCR amplification process that is necessary for the method used in the art.

What is claimed is:

1. An electrochemical microarray chip for analyzing target molecules in a solution, comprising:
    at least two electrically isolated electrodes on the chip exposed to the solution;
    each electrode having an array of at least two microspots comprised of immobilized probe molecules;
    electronic circuitry connected to the electrodes to apply an oscillatory potential relative to the solution to each electrode independently;
    means to regulate the amount of specific binding of the target molecules in the solution to the probe molecules by controlling the oscillatory potential relative to the solution to each electrode; and
    at least one redox ion disposed in the solution that exchanges electrons with the electrode during the oscillatory potential.

2. The microarray chip as claimed in claim 1, further including means to apply a light beam to the microspots on the electrodes and means to measure the amplitude of oscillation of reflectivity of the light beam from each microspot as a function of applied oscillatory potential.

3. The microarray chip as claimed in claim 2 wherein the electrode has reflectivity of at least 50% at the wavelength of the applied light.

4. The microarray chip as claimed in claim 1 wherein each microspot has a sequence of immobilized single-stranded DNA (ssDNA), ssRNA, or PNA with 10 to 1000 bases.

5. The microarray chip as claimed in claim 1 wherein the probe molecules are immobilized to the electrode by a terminal thio-group.

6. The microarray chip as claimed in claim 1 wherein on the electrode surfaces are modified by a polyelectrolyte with at least one of amine groups, aldehyde groups, carboxylic groups and hydroxyl groups to immobilize the probe molecules.

7. The microarray chip as claimed in claim 1 wherein the microspots are patterned on the electrode by a photolithography process.

8. The microarray chip as claimed in claim 1 wherein the array of microspots on each electrode have at least two different sequences of probe molecules.

9. The microarray chip as claimed in claim 1 wherein the solvent of the solution is an organic solvent that can dissolve ions.

10. The microarray chip as claimed in claim 1 wherein the electrodes are comprised of at least one of: Au, Pt, Ag Re, Rh, and Ru, and their alloys.

11. The microarray chip as claimed in claim 1 wherein the redox ion has a redox potential that is positive.

12. The microarray chip as claimed in claim 1 wherein the range of oscillatory potential ranges from positive to oxidize at least some of the redox ions and to negative potential to regenerate the electrode interface by reducing the redox ions back and repelling the target molecules that did not bind specifically.

13. The microarray chip as claimed in claim 1 wherein the solution includes dyes that can exhibit redox current.

14. The microarray chip as claimed in claim 1 wherein each microspot has a sequence of immobilized single-stranded DNA (ssDNA), ssRNA, or PNA with 10 to 200 bases.

15. The microarray chip as claimed in claim 2 wherein the electrode has reflectivity of at least 90% at the wavelength of the applied light.

* * * * *